(12) United States Patent
Bao et al.

(10) Patent No.: US 6,224,630 B1
(45) Date of Patent: *May 1, 2001

(54) IMPLANTABLE TISSUE REPAIR DEVICE

(75) Inventors: Qi-Bin Bao, Bloomington, MN (US); Hansen A. Yuan, Fayetteville, NY (US)

(73) Assignee: Advanced Bio Surfaces, Inc., Minnetonka, MN (US)

(*) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/086,848

(22) Filed: May 29, 1998

(51) Int. Cl.⁷ .................. A61F 2/44; A61F 2/28
(52) U.S. Cl. .................. 623/17; 623/16
(58) Field of Search .................. 623/11, 16, 17

(56) References Cited

U.S. PATENT DOCUMENTS

| | | |
|---|---|---|
| 1,995,970 | 3/1935 | Dorough . |
| 2,609,347 | 9/1952 | Wilson . |
| 2,653,917 | 9/1953 | Hammon . |
| 2,659,935 | 11/1953 | Hammon . |
| 2,664,366 | 12/1953 | Wilson . |
| 2,664,367 | 12/1953 | Wilson . |
| 2,676,945 | 4/1954 | Higgins . |
| 2,683,136 | 7/1954 | Higgins . |
| 2,703,316 | 3/1955 | Schneider . |
| 2,758,987 | 8/1956 | Salzberg . |
| 2,846,407 | 8/1958 | Wilson . |
| 2,951,828 | 9/1960 | Zeile . |
| 3,531,561 | 9/1970 | Trehu . |
| 4,224,413 | 9/1980 | Burbidge . |
| 4,834,757 | 5/1989 | Brantigan . |
| 5,047,055 | 9/1991 | Bao et al. . |
| 5,171,281 | 12/1992 | Parsons et al. . |
| 5,258,043 | 11/1993 | Stone . |
| 5,354,736 | 10/1994 | Bhatnagar . |
| 5,425,772 | 6/1995 | Brantigan . |
| 5,489,307 | * 2/1996 | Kuslich et al. .................. 623/17 |
| 5,492,697 | 2/1996 | Boyan et al. . |
| 5,514,180 | 5/1996 | Heggeness et al. . |
| 5,534,028 | * 7/1996 | Bao et al. .................. 623/17 |
| 5,549,679 | * 8/1996 | Kuslich .................. 623/17 |
| 5,556,429 | 9/1996 | Felt . |
| 5,702,449 | * 12/1997 | McKay .................. 623/17 |
| 5,716,404 | 2/1998 | Vacanti et al. . |
| 5,716,413 | 2/1998 | Walter et al. . |
| 5,755,797 | * 5/1998 | Baumgartner .................. 623/17 |
| 5,842,477 | 12/1998 | Naughton et al. . |
| 5,895,426 | * 4/1999 | Scarborough et al. .................. 623/17 |

FOREIGN PATENT DOCUMENTS

| | | |
|---|---|---|
| 0 614 650 | 9/1994 | (EP) . |
| 0 700 671 | 3/1996 | (EP) . |
| 0 875 219 | 11/1998 | (EP) . |
| WO9726847 | 7/1977 | (WO) . |
| WO 92/03125 | 3/1992 | (WO) . |
| WO 94/23671 | 10/1994 | (WO) . |
| WO 95/07668 | 3/1995 | (WO) . |
| WO9530388 | 11/1995 | (WO) . |
| WO 96/10428 | 4/1996 | (WO) . |
| 9720874 | 5/1998 | (WO) . |

OTHER PUBLICATIONS

Kamblin et al., Development of Degenerative Spondylosis of the Lumbar Spine after Partial Discectomy, *Spine*, 20(5) (1995) pp. 599–607.

(List continued on next page.)

*Primary Examiner*—Michael J. Milano
*Assistant Examiner*—Hieu Phan
(74) *Attorney, Agent, or Firm*—Fredrikon & Byron, P.A.

(57) ABSTRACT

A surgical device and related method and kit for use in sealing a biological aperture in situ. In one embodiment, the device is provided in the form of an expandable, porous material such as poly(vinyl alcohol).

61 Claims, 7 Drawing Sheets

OTHER PUBLICATIONS

Hampton et al., Healing Potential of the Annulus Fibrosus, *Spine*, 14(4) 1989, pp. 398–401.

Burg et al., "Modulation of Surface and Bulk Properties of Biomedical Polymers", *Annals New York Academy of Sciences*, 831 (1997) pp. 217–222.

Cobey, Milton C., Anthroplasties Using Compressed Ivalon Sponge "Intramedic Sponge", *Clinical Orthopaedics and Related Research*, No. 54 (Sep–Oct 1967) pp. 139–144.

Kusaka et al., "The Effect of Annulus Fibrosus Perforation of the Intradiscal matrix Strain of the Axially Loaded Intervertebral Disc", *Transactions of the 44$^{th}$ Annual Meeting of the Orthopedic Research Society*, New Orleans, LA, Abstract 190–32, (Mar. 1998).

Osti et al., Annular Tears and Disc Degeneration in the Lumbar Spine, *Journal of Bone and Joint Surgery*, 74–B(5), Sep. 1992 pp. 678–682.

Osti et al., Annulus Tears and Intervertebral Disc Degeneration, *Spine*, 15(8) (1990) pp. 762–767.

Liu, et al., "Morphologic Characterization of Polyvinyl Sponge (Ivalon) Breast Prosthesis", Arch. Pathol. Lab Med., 120, 1996, pp. 876–878.

Unipoint Industries, Inc. "Polyvinyl Alcohol Foam for Surgical and Industrial Use" Data Sheets.

Silver et al., "Cartilage Wound Healing", Oto. Clin. N.Am., 28(5) 1995, pp. 847–863.

Malemud, "The Role of Growth Factors in Cartilage Metabolism", Rheum. Dis. Clin. N.Am., 19(3) 1993, pp. 569–580.

"Vinyl Alcohol Polymer", pp. 1233–1236 in Kroschwitz, ed., *Concise Encyclopedia of Polymer Science and Engineering*, Wiley & Sons, 1990.

Dodge, et al., "Use of Polyvinyl Sponge in Neurosurgery", Section of Neurologic Surgery and Section of Surgical Research, Mayo Clinic and Mayo Foundation, Nov. 25, 1953, pp. 258–261.

Edgerton, et al., "Augmentation Mammaplasty", *Plastic and Reconstructive Surgery*, vol. 21, Apr. 1958, pp. 279–305.

Peters, et al., "Ivalon Breast Prostheses: Evaluation 19 Years after Implantation", *Plastic and Reconstructive Surgery*, vol. 67, Apr. 1981, pp. 514–518.

Southwick et al., Prosthetic Replacement of Chest–Wall Defects, *A.M.A. Archives of Surgery*, vol. 72, 1956, pp. 901–907.

\* cited by examiner

IMPLANTABLE TISSUE REPAIR DEVICE

FIELD OF THE INVENTION

The invention relates to the field of implantable medical devices, and more particularly, relates to the field of tissue repair, such as methods and materials for repair of the intervertebral disc.

BACKGROUND OF THE INVENTION

Various tissue sites within the human body are susceptible to injury, deterioration and disease. Tissues located at orthopedic joints, organs and various connective tissues are often damaged as a result of injury or surgical procedures, often producing ruptures and apertures in the tissue. For example, such apertures (e.g., the surgical opening and/or removal of tissue) can be created as a result of herniation or biopsy locations. Short-term and long-term structural and functional integrity of tissue is often an important consideration in arthroscopic surgery, especially in those situations where the apertures are slow to close and heal.

The intervertebral discs, which are located between adjacent vertebrae in the spine, provide structural support for the spine as well as the distribution of forces exerted on the spinal column. An intervertebral disc consists of three major components: cartilage endplates, nucleus pulposus, and the annulus fibrosus. The central portion, nucleus pulposus, is relatively soft and gelatinous, being composed of about 70 to 90% water. It has a high proteoglycan content and contains a significant amount of Type II collagen and chondrocytes. Surrounding the nucleus is the annulus fibrosus, which has a more rigid consistency and contains an organized fibrous network of approximately 40% Type I collagen, 60% Type II collagen, and fibroblasts. The annular portion serves to provide peripheral mechanical support to the disc, afford torsional resistance, and contain the softer nuclear portion and resist its hydrostatic pressure. A number of other functions which the annulus fibrosus can perform are discussed in Kusaka et al., "The Effect of Annulus Fibrosus Perforation of the Intradiscal matrix Strain of the Axially Loaded Intervertebral Disc", *Transactions of the 44th Annual Meeting of the Orthopedic Research Society*, New Orleans, La., Abstract 190-32, (March 1998).

Intervertebral discs are, however, susceptible to a number of injuries. Disc herniation occurs when the nucleus begins to extrude through an opening in the annulus, often to the extent that the herniated material impinges on nerve roots in the spine. The posterior and posterio-lateral portions of the annulus are most susceptible to attenuation or herniation, and therefore, the most vulnerable to the hydrostatic pressures exerted by vertical compressive forces on the intervertebral disc. Various injuries and deterioration of the intervertebral disc and annulus fibrosus are discussed by Osti et al., Annular Tears and Disc Degeneration in the Lumbar Spine, Journal of Bone and Joint Surgery, 74-B(5), September 1992 pp. 678–682; Osti et al., Annulus Tears and Intervertebral Disc Degeneration, *Spine*, 15(8) (1990) pp.762–767; Kamblin et al., Development of Degenerative Spondylosis of the Lumbar Spine after Partial Discectomy, *Spine*, 20(5) (1995) pp. 599–607.

Many treatments for intervertebral disc injury have involved the use of nuclear prostheses or disc spacers. A variety of prosthetic nuclear implants are known in the art. For example, see Bao et al., U.S. Pat. No. 5,047,055, which teaches a swellable hydrogel prosthetic nucleus. Other devices known in the art, such as intervertebral spacers, use wedges between vertebrae to reduce the pressure exerted on the disc by the spine. Intervertebral disc implants for spinal fusion are known in the art as well, as taught by Brantigan, U.S. Pat. Nos. 5,425,772 and 4,834,757. In spite of these advances in treating the overall disc, remaining problems include the effective repair or restructuring of annular tissue, per se. This is true regardless of whether the annular tissue has been damaged by herniation, or by the creation of surgical access ports in the course of disc repair. This is primarily due to the avascular nature of the annulus, and partly due to the difficulties associated with hydrostatic pressure exerted on the entire disc by the compressive forces on the spine. For example, see Hampton et al., Healing Potential of the Annulus Fibrosus, *Spine*, 14(4) 1989, pp.398–401 which discusses some of the difficulties encountered in such repairs.

On a separate subject, natural and synthetic porous materials which enhance or encourage natural tissue growth are known in the art. For example, see Burg et al., "Modulation of Surface and Bulk Properties of Biomedical Polymers", *Annals New York Academy of Sciences*, 831 (1997) pp.217–222; and Vacanti et al., U.S. Pat. No. 5,716,404. A number of implantable devices that involve the use of expandable materials are also known. For example, Cobey, Milton C., "Arthroplasties Using Compressed Ivalon Sponge ("Intramedic Sponge", *Clinical Orthopaedics and Related Research*, No.54 (September–October 1967) pp. 139–144 teaches an implantable plastic sponge material used on joint surfaces which induces fibrous tissue ingrowth. See also Stone, U.S. Pat. No. 5,258,043, which teaches a prosthetic intervertebral disc that functions as a scaffold for tissue ingrowth.

On yet another subject, Applicant has described prosthetic implants formed of biomaterials that can be delivered and cured in situ using minimally invasive techniques. See, for instance, Applicant's U.S. Pat. No. 5,556,429, and published International Application WO 95/30388. Applicant's published International Application WO 97/26847 and International Application No. PCT/US97/20874, filed Nov. 14, 1997, (the disclosures of each of which are incorporated herein by reference) further describe, inter alia, the formation of a prosthetic nucleus within an intervertebral disc by a minimally invasive method that includes, for instance, the steps of inserting a collapsed balloon mold prosthesis through a cannula that is itself positioned through an opening within the annulus, and filling the balloon with a flowable biomaterial that is adapted to cure in situ and provide a permanent disc replacement.

Although a number of prosthetic intervertebral discs, nuclear implants, and disc spacers are known in the art, relatively little attention has been focused on effectively sealing an opening in the annulus which has either been initiated surgically, such as an access port for a minimally-invasive technique, or caused naturally, as in the case of herniation.

SUMMARY OF THE INVENTION

The present invention provides a device and related method for sealing biological apertures (e.g., orifices, holes, clefts, tears, and openings) in situ, such as an annular tear or disc herniation site, the device comprising a material adapted to be sealably positioned within the aperture and to permit natural tissue ingrowth, such as fibrous tissue ingrowth, into the device. Preferably, the material is porous and adapted to be delivered to and positioned within the aperture, in conformity with the dimensions of the aperture, using minimally invasive techniques. In a preferred embodiment, the porous material is adapted to become permanently secured over time, by permitting, or more preferably actively facilitating, ingrowth of natural fibrous tissue into some or all of the pores. Such ingrowth can be facilitated, for instance, by providing an optimal combination of porosity and bioactivity (e.g., surfaces or portions having bioactive factor(s) incorporated therein).

The material is expandable, such that once positioned the material can swell (e.g., by hydration or release of constraining means) in order to initially secure the expanded device within the aperture. The device itself can be permanent (e.g., non-biodegradable) or temporary (e.g., removable or biodegradable), in whole or in part. The device can be provided in a variety of configurations, e.g., in the form of a generally cylindrical plug, or in tubular or sheet-like form. The particular configuration (e.g., shape and dimensions) of a device will typically be adapted to its intended use. In a particularly preferred embodiment, the biological aperture is an opening located in the annulus of the intervertebral disc, and the porous, expandable material is poly(vinylalcohol) ("PVA") and shaped in the form of a generally cylindrical plug.

The invention further provides kits, and components therefore, for use in performing a surgical method as described herein, as well as other surgical instruments and devices that themselves adapted for use with, or incorporate, a device as described herein. In addition to the benefits and advantages described herein, the method and device of the present invention are particularly adapted for use with minimally invasive surgical techniques.

BRIEF DESCRIPTION OF THE DRAWING

The invention will be further illustrated in the accompanying Drawing and description as follows.

DETAILED DESCRIPTION OF THE INVENTION

As used herein the following terms are defined as follows:

The word "aperture" and term "biological aperture" will be used interchangeably to refer to any opening, slit, etc., within a bodily tissue, whether formed as a result of injury, deterioration, disease, or surgery, which would benefit from repair or closure. Apertures can occur naturally or through disease or injury in tissue sites of organs, joints, bone, and connective tissue, e.g. tendons, ligaments, capsular ligaments, and the like, or can be formed as the result of biopsy or excision.

The term "tissue ingrowth" will refer to the growth of autologous or heterologous tissue, including tissue from any of the following sources: 1) the patient's own natural tissue (e.g., surrounding the aperture itself), 2) tissue from another site that is transplanted to the site, ( e.g., covering the device), and 3) cells seeded into the device as described herein. Such ingrowth can be natural and/or induced. Tissue growth can occur, for instance, as a natural healing response to the presence of a device as described herein, and/or in response to the use of bioactive agents, such as growth factors and the like.

The word "expandable", and inflections thereof, as used with regard to the present device, will refer to a material that can be deformed (e.g., constricted) with regard to one or more of its original dimensions, e.g., by dehydration or compression, and having sufficient resilience to substantially recover its original (hydrated or uncompressed) dimensions upon release or negation of the deformation.

The term "porosity", and inflections thereof, as used with regard to a device of the present invention, will refer to a three-dimensional structure that permits or facilitates tissue ingrowth when placed within the body. Such three-dimensional structures include matrices such as open cells or channels, fibrous structures, textures having increased surface area, and the like.

The term "minimally invasive", as used with respect to the present method, will refer to surgical techniques and associated instruments, such as arthroscopic surgical instruments, having structural dimensions which produce minimal trauma to the patient's tissue.

The invention relates to a device and method (e.g., minimally invasive method) for sealing biological apertures in situ, such as an annular tear or disc herniation site. A preferred device comprises a material which permits tissue ingrowth, such as fibrous tissue, into the material from the tissue immediately surrounding the aperture. Preferably, the material is porous and adapted to be delivered to and positioned within the aperture, using minimally invasive techniques, in conformity with the dimensions of the aperture. The porous material is adapted to be permanently secured by permitting (or more preferably actively facilitating) the ingrowth of natural fibrous tissue into some or all of the pores, e.g., by an optimal combination of porosity and bioactivity (e.g., surfaces or portions having bioactive factor(s) incorporated therein).

The material can also be expandable so that once in position, the material can increase in one or more dimensions (e.g., swell by hydration or expand upon release of constraining means) in order to afford initial securing of the device within the aperture. In a particularly preferred embodiment, the device is in the shape of a cylindrical plug and is adapted for placement into an opening located in the annulus of the intervertebral disc, wherein the material of the device is a polyvinyl alcohol formulation which is both porous and expandable.

The device can be placed in any suitable tissue site containing an aperture which would benefit from autologous or heterologous tissue ingrowth for healing. Typically, such apertures are produced as a result of injury (e.g., herniation) or created surgically, such as at biopsy sites, as access apertures for surgical instruments (e.g. catheter), or insertion of an implant, for example. Tissues having such apertures include both vascularized and non-vascularized tissue.

Because of the lack of vascular access, non-vascularized tissue sites, such as that of the annulus of the intervertebral disc, are typically far more difficult to heal. Non-vascularized tissue sites, particularly those prone to herniation, tend to benefit from immediate and secure closure and are particularly suited for the device of the invention.

The healing process of the intervertebral disc annulus, in particular, can be facilitated by enhancing fibrous tissue growth. Apertures located in the annular portion of the disc are susceptible to significant hydrostatic or other pressures. The device and method of the invention is particularly suited for repair of the intervertebral disc, where the failure to heal or herniation through such apertures poses a risk for further damage. Accordingly, by using the device of the invention, the aperture in the annulus can be sealed and biocompatibility of the implant assured, while the disc itself is provided with sufficient short- and long-term mechanical support and function.

Figure 1:
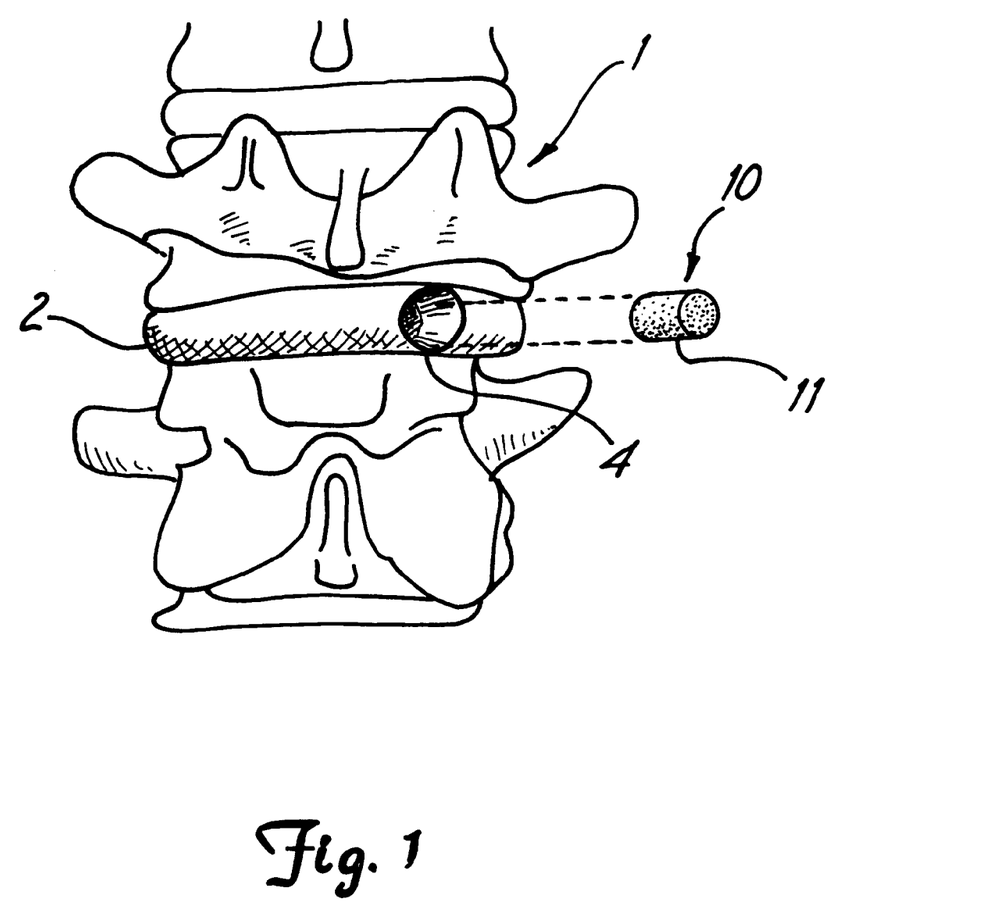
FIG. 1 is an overall schematic depiction of a portion of the spine wherein a device of the present invention is positioned within an annular aperture in the intervertebral disc.
Figure 2:
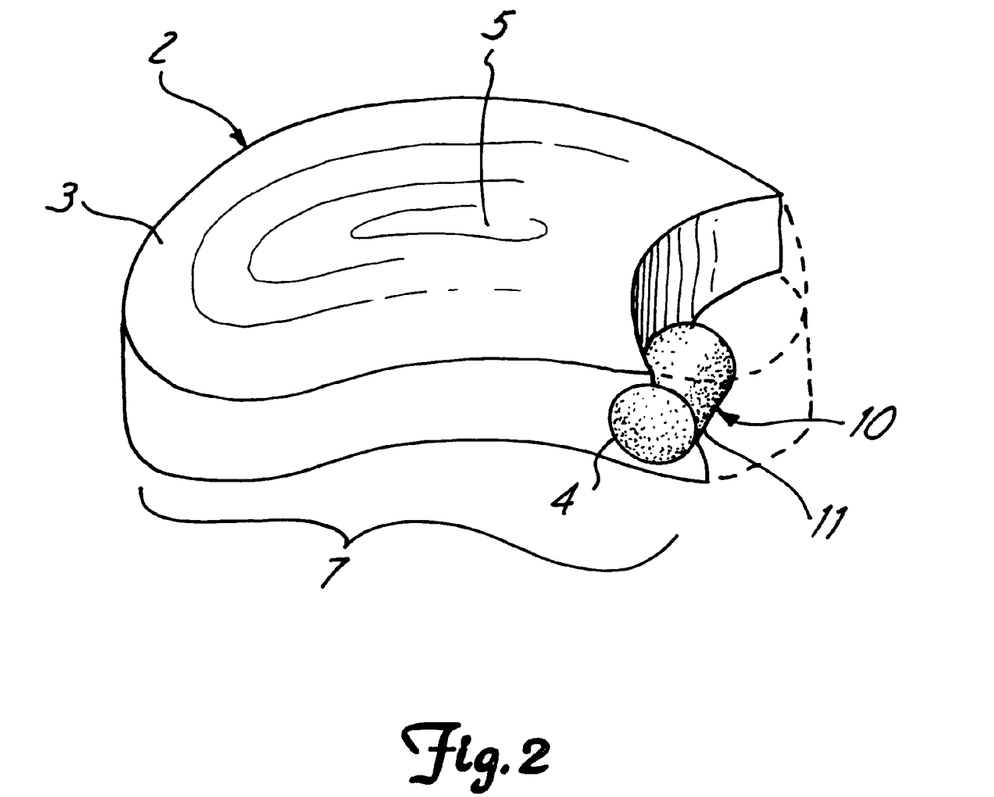
FIG. 2 is a cut-away view from an angled perspective of the intervertebral disc containing the device positioned in situ according to one embodiment of the invention.

As can be seen from FIGS. 1 and 2, the device 10 is illustrated as being adapted for insertion into the intervertebral disc 2 of the spine 1. In particular, the device 10 is adapted for insertion into an aperture 4 located in the annular portion 3 of the disc 2 such that the peripheral surface 11 of the device 10 contacts the intact tissue surrounding the aperture 4 thereby both sealing the annulus 3 in a manner sufficient to prevent extrusion of the inner material of the nucleus 5, and to inhibit migration of the device within or from its placed position.

A preferred device of the invention includes at least one material that is sufficiently porous to permit tissue ingrowth into the material from surrounding tissue of the implant site. Suitable materials for use with the device of the invention include, but are not limited to, natural or synthetic polymers and co-polymers, plastics, metallic materials and alloys, ceramics, and the like. Preferred materials provide a surface porosity, e.g., in the form of a fibrous matrix or pores themselves, sufficient to permit tissue ingrowth into the material. Most preferred are those natural and synthetic polymers, co-polymers and combinations that can be processed into the form of porous matrices (e.g., webs) or foams. Examples of foamable synthetic polymers include, but are not limited to, polyvinyl alcohol (PVA), polyethylene (PE), polyurethane (PU), polypropylene (PP), nylon, polycaprolactone (PCL), and copolymers and combinations thereof.

When one or more non-biodegradable materials are used in the device, preferred are those polymers and co-polymers that can be processed into expandable, porous structures (e.g., swellable matricies or foams). Examples of synthetic non-biodegradable polymers, include, but are not limited to, various polyacrylates, ethylene-vinyl acetates (and other acyl-substituted cellulose acetates), polyurethanes, polystyrenes, polyvinyl oxides, polyvinyl fluorides, poly (vinyl imidazoles), chlorosulphonated polyolefins, polyethylene oxides, polyvinyl alcohols (PVA), polytetrafluoroethylenes and nylons.

A particularly preferred material for use in the device is polyvinyl alcohol (PVA) and alkylated or acylated derivatives thereof. See, for instance, "Vinyl Alcohol Polymer", pp. 1233–1236 in Kroschwitz, ed. *Concise Encyclopedia of Polymer Science and Engineering,* Wiley & Sons, 1990, the disclosure of which is incorporated herein by reference. Non-biodegradable polyvinyl alcohol sponges are commercially available from Unipoint Industries (IVALON). A suitable processes for making porous polyvinylalcohol are described in Wilson, U.S. Pat. Nos. 2,609,347, 2,664,366, 2,664,367, 2846,407 and Hammon U.S. Pat. Nos. 2,653,917, 2,659,935, the disclosures of each of which are incorporated herein by reference.

Generally, polymers can be provided in the form of an expandable foam using conventional foam generation techniques available in the art. Accordingly, foams can be produced by infiltrating the materials with gasses, dissolving gasses into the materials, introduction of gasses into the medium by static or moving gas inlets, and the like. A foam can be produced by using any suitable non-toxic gas or mixtures thereof.

Preferred biodegradable materials include natural and synthetic matricies and foams. More preferred biodegradable materials for use in the device are those which can be processed into polymeric matrices or foams, such as collagen. Biodegradable materials are particularly suitable in applications where it is desired that natural tissue growth be permitted to completely or partially replace the implanted material over time. Accordingly, biocompatibility is ensured and the natural mechanical parameters of the tissue are substantially restored to those of the pre-damaged condition.

Examples of synthetic biodegradable polymers include, but are not limited to, polylactides (PLA), polyglycolic acids (PGA), poly(lactide-co-glycolides) (PLGA), polycaprolactones (PCL), polycarbonates, polyamides, polyanhydrides, polyamino acids, polyortho esters, polyacetals, polycyanoacrylates, and degradable polyurethanes. Examples of natural biodegradable polymers include, but are not limited to, albumin, collagen, synthetic polyamino acids, prolamines, polysaccharides such as alginate, heparin, other biodegradable polymers of sugar units. Synthetic biodegradable polymers and their preparation, in particular polylactides, are taught by Dorough, U.S. Pat. No. 1,995, 970; Schneider U.S. Pat. No. 2,703,316; Salzberg U.S. Pat. No. 2,758,987; Zeile, U.S. Pat. No. 2,951,828, Higgins, U.S. Pat. No. 2,676,945, Trehu U.S. Pat. Nos. 2,683,136, 3,531, 561, the disclosures of each of which are incorporated herein by reference.

Examples of natural fibrous biodegradable polymers include, but are not limited to, collagen, elastin, and reticulin. Most preferred as the fibrous material are collagen fibers. Fibrous materials suitable for use in the invention can be prepared by various techniques, such as crosslinking as taught by Stone, U.S. Pat. No. 5,258,043, the entire text of which is incorporated herein by reference.

Preferred biodegradable materials are adapted to retain their structural integrity, in situ, for a period of time in order to permit substantial tissue ingrowth into the device. For purposes of the invention, the time period to permit substantial tissue ingrowth typically comprises at least about 4 weeks, more typically a range of from about 4 weeks to about 6 months.

The biodegradation kinetics (e.g., rate and extent of tissue ingrowth) can be altered or controlled by various methods and techniques known in the art, such as modification of the physical and/or chemical properties of the material. For example, the material can be coated or otherwise treated so as to delay degradation of the material. Average molecular weights of polymeric materials can also be altered in order to modify degradation kinetics. The degradation kinetics of certain polymers, such as polylactic acid, polyglycolic acid, or co-polymers thereof, can be altered by increasing average molecular weight. Structural integrity of such polymeric materials can be significantly prolonged by higher average molecular weights of approximately 90,000 daltons or higher, as compared to shorter term degradation molecular weights of approximately 30,000 daltons or less.

Intimate natural tissue ingrowth into the device, such as that of fibrous tissue growth, can be accomplished by optimizing one or more porosity parameters of the material. Accordingly, a preferred material used in the device exhibits a porosity sufficient to permit natural ingrowth of tissue. Preferably, the porosity parameters are sufficient to facilitate fibroblast ingrowth so as to result in fibrous tissue ingrowth. Porosity parameters of the material can be selected and modified in order to optimize natural tissue ingrowth into the device. By selecting the appropriate parameters (e.g., pore size, structure and distribution) natural tissue growth into the material can be optimized. In a further embodiment, the device can contain a plurality of portions, each exhibiting one or more different parameters, e.g., in order to permit different kinetics of desired cell ingrowth into the device.

Particular parameters of pore size and structure in certain biomaterials have been associated with optimal tissue ingrowth. A preferred material has a pore size and structure adapted to allow free exchange of nutrients and gasses to the cells integrated into the material. For purposes of the invention, pore sizes can range, for instance, from about 50 microns to about 500 microns, preferably from about 100 to about 300 microns. The porosity parameters can be varied according to different tissue types and associated porosity-induced tissue ingrowth therein. In annular tissue, for example, the pore size of the material is that which is associated with ingrowth of fibroblasts.

In an alternative embodiment, the material of the device can induce tissue ingrowth by virtue of a fibrous architecture. The material can comprise a fibrous matrix sufficient to permit the patient's own tissue ingrowth into the material. The fibrous matrix structure can be in the form of a fibrous mesh or scaffold, or interwoven fibrils, wherein the fibrous material comprises a natural or synthetic polymeric material as described herein. Preferably, the fibrous configuration is such that free exchange of nutrients and gases is allowed to the cells while integrated on the matrix. Typically, the space between fibers is in the range of from about 10 microns to about 1000 microns, preferably about 50 microns to about 400 microns, and most preferably from about 100 microns to about 300 microns.

Figure 3:
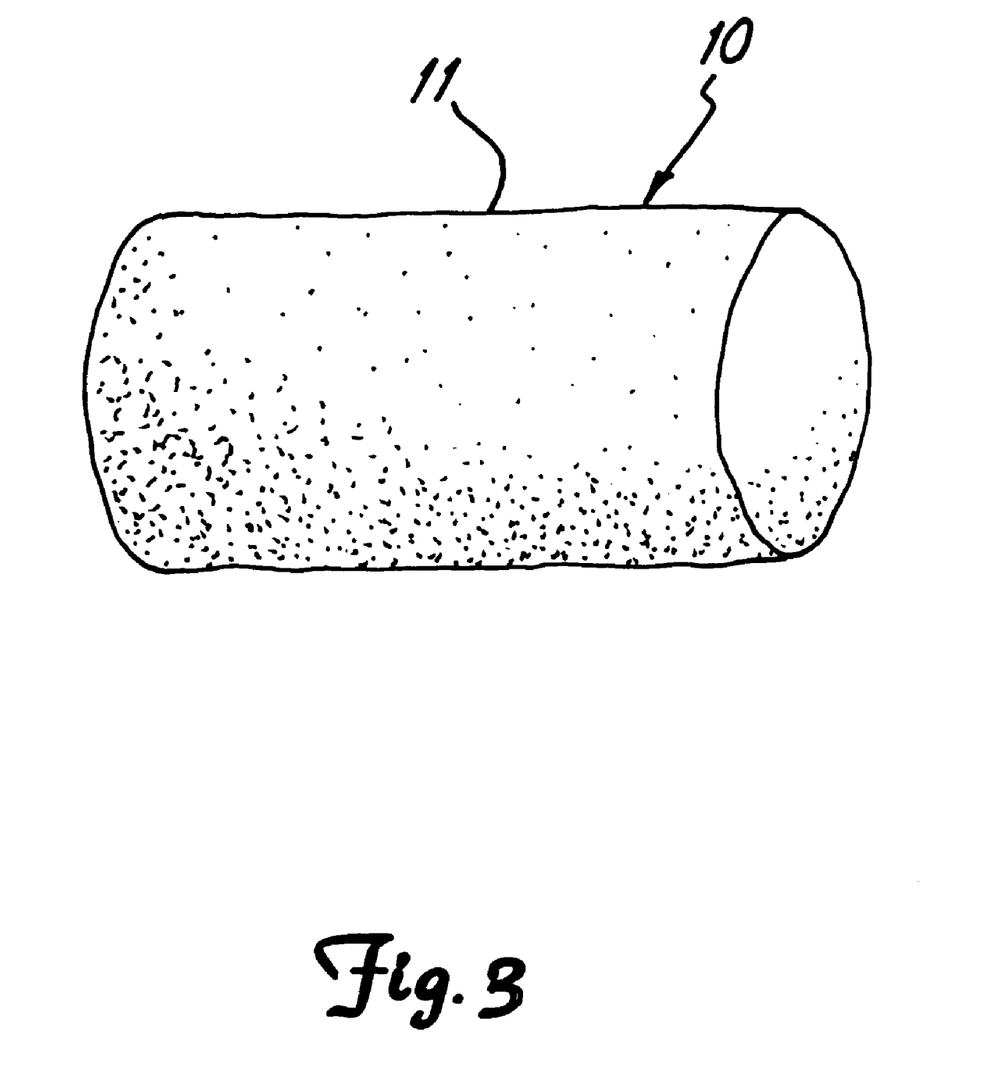
FIG. 3 is an enlarged side view of the device of the invention in a plug configuration.

The device is provided in a configuration sufficient to provide a secure, compliant fit, given the dimensions of the biological aperture within which it is placed. An optimal configuration (e.g. shape and dimensions) of the device can be determined based upon the natural and/or desired geometry of the implant site. The device configuration can be modified according to particular dimensions of the aperture and/or particular desired functional requirements. For example, when used to repair a circular aperture 4 as depicted in FIGS. 1 and 2, the device 10 can be in the shape of a generally cylindrical plug as illustrated in FIG. 3. Alternatively, the device can have a cubic, elongated (e.g., strand-like), hollow tubular, or sheet-like form depending upon the desired tissue site. The device can be sculpted or molded into a desired configuration using conventional techniques.

A device can have other structural features unique to its application. For instance, a cylindrical plug, for use in sealing an annular aperture, can be provided with one or more expanded or enlarged end portions (forming a mushroom-, spool-like or anvil-like configuration) in order to prevent migration of the plug and better contain nuclear material. The plug can be provided, for instance, with its interior end enlarged, or adapted to expand disproportionately more than the barrel, such that the interior portion forms an internal lock upon insertion, thereby preventing movement of the device or extrusion of the nucleus. Expansion of the annular plug device results in a taught circumferential sealing of the access port. Accordingly, the device can induce further tissue ingrowth into the nuclear region as well as the peripheral annular region so as to provide further mechanical support to the disc.

Numerous techniques (e.g., selection, shaping, sculpting or molding techniques) can be used in order to configure a device for a particular implant site, depending largely upon the aperture itself and the particular material used. When porous polyvinyl alcohol (PVA) is used as the material for the device, suitable techniques include cutting and heat molding. Accordingly, the porous PVA material can be cut or carved using a knife or scissors. Porous PVA also tends to exhibit thermoplastic properties when saturated with water, which enables the material to be configured by heat molding it into various dimensions and shapes upon heating and/or drying. A preferred heat molding process for porous PVA generally includes the steps of a) wetting the material, b) cutting or sculpting the wetted material to a shape and dimension which is between about 10% and about 30% larger than that of the desired final form (when heat treated, porous PVA tends to permanently lose approximately 20% of its original size), c) encasing the material into a mold having the desired configuration, d) immersing the mold-encased material into boiling water or steam, e) subsequently cooling the mold-encased material, and finally, f) removing the material from the mold.

The device of the invention can be provided having a configuration that best accommodates the dimensions of an aperture into which it is positioned, such as an annular herniation or access aperture. It is generally desirable for the device to fit securely in, as well as penetrate into, and preferably through, the annulus to the extent desired. The normal height of an intact annulus at its periphery is approximately one centimeter, although this varies according to the individual patient and tends to become smaller with age and can be affected by injury or compressive damage to the disc.

As illustrated in FIGS. 1 and 2, when implanted into an annulus 3, a device 10 is generally cylindrical in configuration, e.g. in the shape of a plug. Accordingly, the width of the expanded device is sufficient to conform to the width of the aperture 4 in the annulus 2, such that the device 10 both seals the annulus in a manner sufficient to prevent extrusion of the inner nucleus material, and to inhibit migration of the device within or from its placed position.

Figure 4:
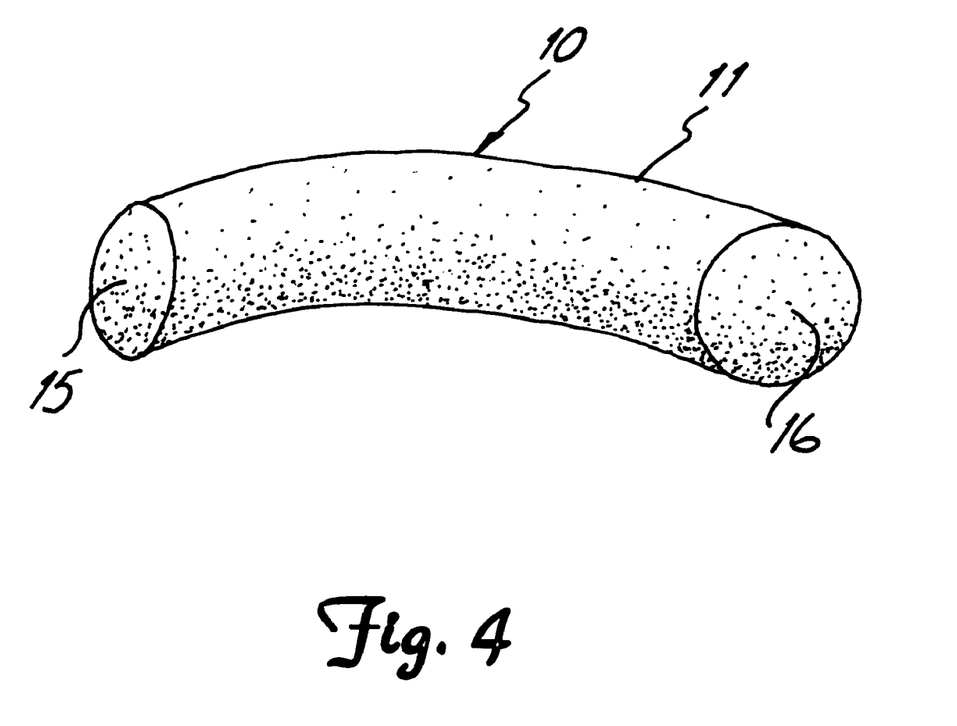
FIG. 4 is an enlarged angled view of an elongated configuration of the device according to one embodiment of the invention.
Figure 5:
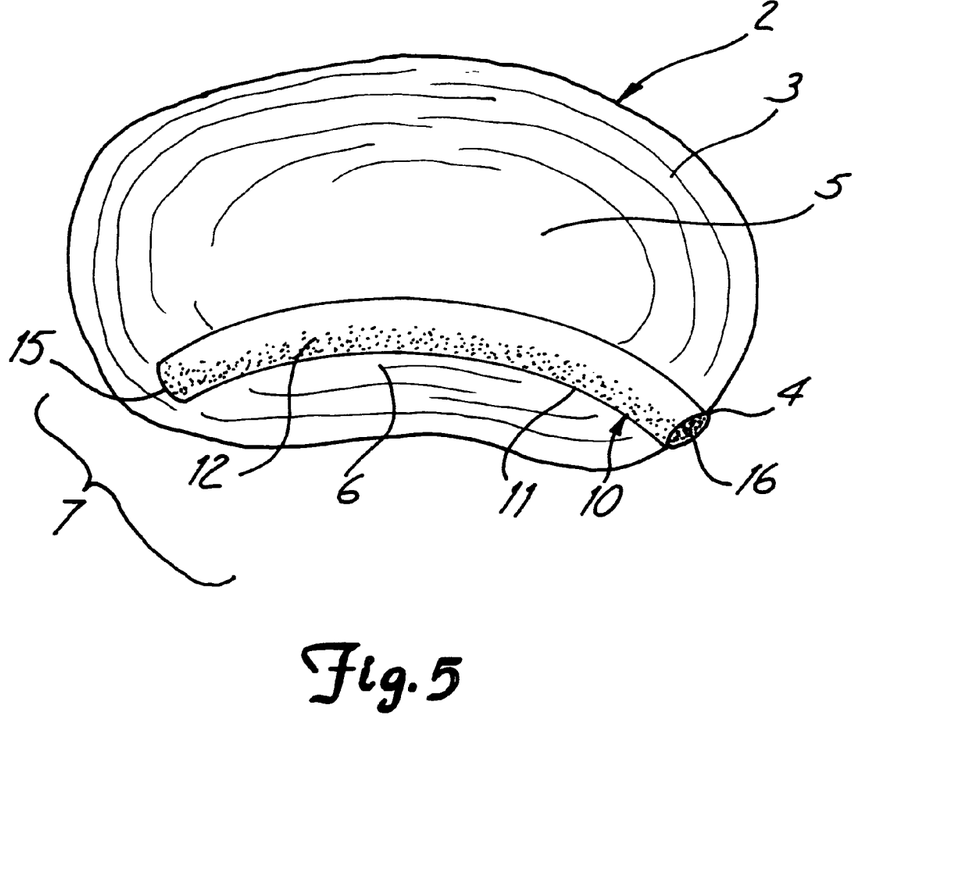
FIG. 5 is a cross-sectional view from a top perspective of an intervertebral disc containing the elongate configuration of the device according to one embodiment of the invention.

Now referring to FIGS. 4 and 5, a device 10 is shown having an elongated configuration having first and second ends 15 and 16, respectively. The device 10 is shown in position within the annulus 3 of a disc 2, with the first end 15 extending along the interior wall 6 of the annulus 3 proximal to the nuclear portion 5. Accordingly, the elongated configuration is adapted for insertion into one opening through the annulus 3 and is provided with a slightly curved portion adapted to reside proximal to and against the interior wall 6 of the annulus 3 between the annulus 3 and the nuclear 5 portion. The elongated structure offers the advantage of providing support to the entire posterior or lateral portion 7 of the annulus, thereby forming an even wider wall or barrier which affords support and prevents herniation over a wider area of the disc 2.

An elongated form of the device can be used in conjunction with a single aperture or plurality of apertures (not shown) within the annulus. When positioned through a single aperture 4, a first end 15 of the device 10 can be anchored or otherwise secured to the interior of the annular wall 6.

Alternatively, the device can contain an elongated configuration adapted for a dual aperture system (not shown) in which each end of the elongated device resides in respective apertures, typically on opposing sides of the annulus. This dual aperture system permits the practitioner to surgically maneuver both ends of the device into the proper position during surgery.

Optionally, or in addition to porosity, one or more bioactive agents can be incorporated into the device, e.g., onto or into the porous material itself and/or one or more other materials making up the device. Bioactive agents suitable for use include natural and synthetic compounds, examples of which are bioactive polypeptides, proteins, cells, and the like, which permit (e.g., stimulate) tissue ingrowth. Preferred bioactive agents are those which actively facilitate tissue ingrowth and/or improve the biocompatibility of the device when used in conjunction with the material of the device.

Suitable bioactive agents include, but are not limited to, tissue growth enhancing substances such as growth factors, angiogenic factors, immune system suppressors such as antiinflamatory agents, antibiotics, living cells, cell-binding proteins and peptides, and the like. Growth factors which enhance cartilage repair are particularly preferred for use as bioactive agents. Examples of suitable growth factors are selected from the group consisting of somatomedins (somatomedin-C), insulin-like growth factors (such as IGF-I and II), fibroblast growth factors (including acidic and basic FGF), bone morphogenic factors (e.g., BMP and BMP2), endothelial cell growth factors, transforming growth factors (TGF alpha and beta), platelet derived growth factors ("PDGF"), hepatocytic growth factors, keratinocyte growth factors, and combinations thereof. Growth factors that function by attracting fibroblasts are preferred, as are growth factors that encourage fibroblast growth, either directly or indirectly by encouraging mesenchymal cell development.

When cell-binding proteins and peptides which may be used, those which enhance cell binding to collagen are preferred. Suitable cell-binding peptides include, but are not limited to, those disclosed in U.S. Pat. No. 5,354,736, the entire disclosure of which is incorporated herein by reference.

The bioactive agent can be either immobilized upon the implanted device and/or it can be released therefrom in situ. Growth factors can be incorporated in a releasable fashion using conventional controlled release methods, including but not limited to encapsulation or microspheres. Selection of the particular bioactive agent(s) for use with the device and the controlled release technique thereof will vary, as those skilled in the art will appreciate, according to the particular implant tissue site.

Suitable bioactive agents also include living cells, which can be incorporated prior to implantation into a porous material. The material, in turn, serves as a cell growth matrix or scaffold in order to enhance tissue ingrowth in vivo. Accordingly, in vitro cell culture techniques, e.g. autograft or allograft techniques, can be used to integrate or embed living cells into the material of the device. Preferably, the patient's own cells are cultured using autograft techniques in order to enhance biocompatibility. Cells incorporated into the material can include cells identical to those of the tissue surrounding the implant site, or those which can differentiate into the same. Examples of cell types which enhance tissue ingrowth include, but are not limited to, fibroblasts, chondrocytes, chondroblasts, osteocytes, mesenchymal cells, epithelial cells, endothelial cells, and the like.

When using in vitro cell culture techniques to enhance tissue ingrowth, preferably the device is provided with the cells prior to implantation. The cells can be harvested from the body and cultured directly on the device or material using standard cell culture methodology. For example, see Burbidge, U.S. Pat. No. 4,224,413, the disclosure of which is incorporated herein by reference. Accordingly, the patient's own living cells can be harvested from the target tissue site or another site containing the same type of cells. For example, when the aperture site is the annulus of a disc, the cells, including human fibroblast cells, can be removed from the annular portion of the disc. The cultures are incubated at a temperature of approximately 37° C. for a time period sufficient to induce cell growth into the device material in a growth or nutrient medium suitable for the particular cell type to be cultured. The medium is buffered to the correct physiological pH range from about 6.5 to about 8.0, preferably from about 7.0 to about 7.2, and can be supplemented with metal salts such as Earle's salts, sodium bicarbonate, ascorbic acid, nonessential amino acids such as alanine, asparagine, aspartic acid, glycine, glutamic acid, proline, serine, or serum such as fetal bovine serum. The medium can also contain antibiotics, such as penicillin or streptomycin. Examples of medium suitable for culturing mammalian cells include Eagle's (MEM), Fischer's , Hamn's , Leibovitz, McCoy's , Neumann and Tytell's , Puck's , Swim's , Trowell's , Waymouth's , 199, NCTC 109, NCTC 135, CMRL 1066, and RPML.

Once the device contains the desired amount of cell ingrowth within the material, the device can be removed from culture and implanted in situ.

Figure 6:
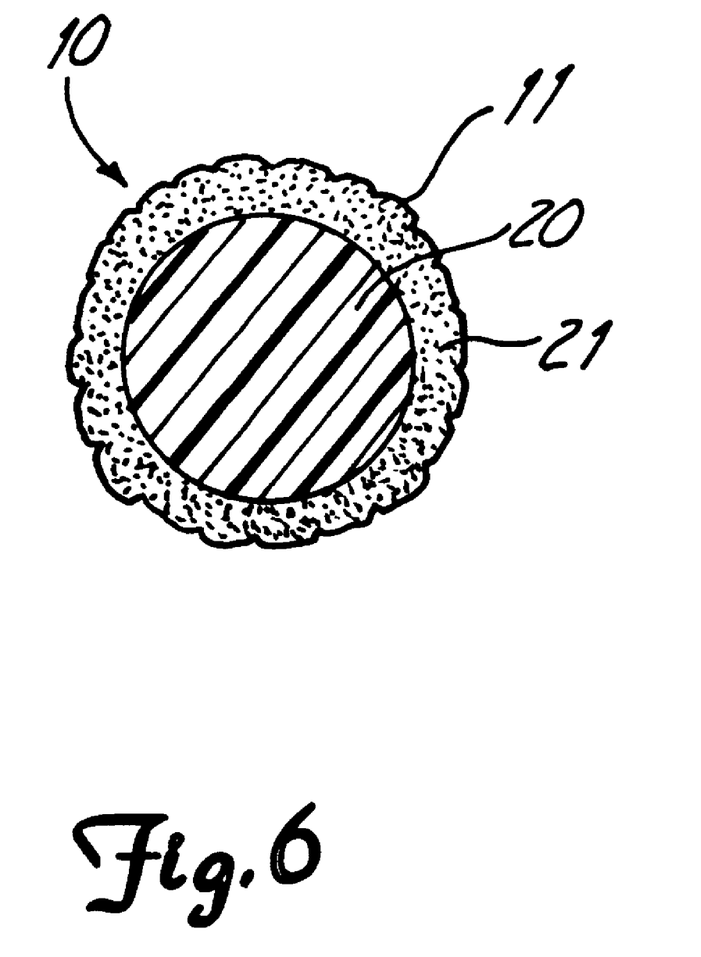
FIG. 6 is a cross-sectional view from a longitudinal perspective of the device containing an interior and exterior portion.

A device can be formed of a single material throughout (which itself is either homogeneous throughout or having regions of varying chemical/physical properties), or it can be formed of one or more materials (e.g., in temporary or permanent attached or touching contact), each having different physical and/or chemical properties. In one embodiment as depicted in FIG. 6, the device 10 includes discrete internal and external portions 20 and 21, respectively, wherein the internal portion 20 is provided in the form of a semi-rigid material used to provide mechanical support. Either or both portions can contain bioactive agents and/or other substances, e.g., to enable device imaging such as radio-opaque materials, to provide varied hydration expansion rates, and the like. Materials useful as the internal portion 20 can include polymers, such as polyethylene, and metals, such as titanium or stainless steel, for example. Composite materials can be used as well, namely composites comprising polymeric foams on the external surface. Materials which permit imaging by MRI or X-ray, for example, can be used as well, offering the advantage of being able to monitor the migration of the device both during surgery and over the long-term.

Examples of materials useful as additional components of the device include, but are not limited to, polymers, plastics, inert metals such as stainless steel, aluminum, titanium, palladium, metallic alloys, insoluble inert metal oxides, phosphates, silicates, carbides, silicon carbide, carbon, ceramics or glass, polycarbonate, polystyrene, epoxyresins, silicone, cellulose acetate, cellulose nitrate, cellophane, PTFE (Teflon), polyethylene terephthalate, polyformaldehyde, fluorinated ethylenepropylene co-polymer, polyphenylene oxide, polypropylene, mica, collagen, and the like.

A device of the present invention can also be used in combination with other prosthetic implant apparatuses or techniques, such as delivery apparatuses or minimally invasive surgical instruments. For example referring now to FIG. 7, the device 10 can be configured and adapted for use as part of a biomaterial delivery cannula 30 for delivery of a nuclear prosthesis 31, such as that disclosed in one or more of Applicant's above-referenced published International Application WO 97/26847. In such an embodiment, the device 10 of the invention can be cylindrical and tubular in form and removably positioned within or upon the interior or exterior surfaces 32 of the delivery cannula 30.

Figure 7:
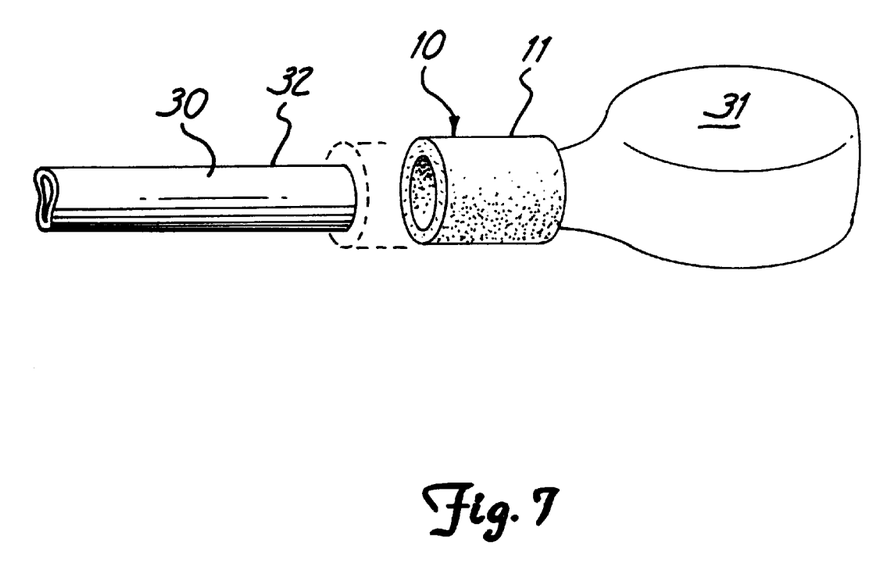
FIG. 7 is a detached depiction of the distal portion of an apparatus for delivering a prosthetic nucleus containing the device according to one embodiment of the invention.

Alternatively, the device of this invention can function as a portion (e.g., distal tip) of the cannula per se (not shown), adapted to be severed from the remainder of the cannula in the course of its use. For instance, upon delivery of a flowable material through the cannula and into the balloon, the cannula can be removed from the tissue site in a manner (e.g., severing the distal tip) that simultaneously seals the access aperture in the annulus. The tip (in the form of a device of the present invention) thereby remains in situ in the surgically created aperture through the annulus to prevent extrusion or herniation of the softer nuclear portion of the disc. Additionally, if an expandable biomaterial is used, the surgically-created access port is sealed after implantation of the prosthesis. Accordingly, the device also facilitates the healing of the annulus after surgery.

The material used in the device of the invention can be either expandable or nonexpandable. Preferably, whatever portion or portions of the device are adapted to directly contact the surrounding tissue implantation site are expandable in situ upon implantation. In their contracted (or unexpanded) form, preferred materials can be adapted for substantially minimally invasive introduction to the tissue site, where upon expansion, they serve to secure the device in place and provide immediate structural support. Upon expansion, a preferred device offers the advantage of being compliant with the aperture, that is, able to substantially conform itself to the shape and dimensions of the aperture, including any irregularities or aberrations in the aperture or implant site. In a related embodiment, a device can be adapted to provide, or tend toward, a predetermined shape and dimensions in its expanded form, thereby serving to determine the corresponding shape of the surrounding tissue.

Preferably, the device is secured within the aperture, at least temporarily, by expansion of the material in situ, e.g., upon hydration or release from constraining means. The extent and kinetics of expansion can be controlled using various methods. For example, hydration expansion of a porous device can be controlled by the use of high molecular weight cross-linking, mechanical compression, chemical additives or coatings, heat treatment, etc. Given the present disclosure, those skilled in the art can select the appropriate method or treatment for controlling expansion according to the particular material used.

Taught and secure positioning of the device within the aperture affords immediate structural support to the tissue. Such support is especially important at tissue injury sites prone to hydrostatic forces, for example the annulus of the intervertebral disc, where the device prevents short-term herniation of the nucleus pulposus from the interior portion of the disc.

Either open surgery or arthroscopic techniques can be used to implant the device. A preferred device of the invention can be implanted under arthroscopic visualization using conventional arthroscopic instruments. The tissue injury site, e.g. the damaged or weakened portion of the intervertebral disc, is accessed and prepared for receipt of the annular device. Using minimally invasive surgical techniques and instruments, the tissue site can be accessed posterio-laterally in conjunction with access ports so as to permit maneuvering of the instruments to prepare the site and implant the device. More than one site on the same tissue, e.g. annulus, can be prepared for a single device or multiple devices, depending upon circumstances. For example, it can be desirable to have two or more plug-shaped devices inserted into the annulus at opposing sides of the disc.

The tissue site is prepared for receipt of the device and the configuration of the device are modified or selected according to the prepared site. For example, the herniated or weakened portion of the annulus are accessed by arthroscopic means and the tissue site prepared. Typically, access to the damaged or deteriorated tissue site will be posterio-lateral access when using arthroscopic techniques. In the case of a herniated disc, the extruded nucleus and surrounding material is removed to the extent necessary to remove the damaged portion. A trocar or any suitable drill configuration which is capable of performing a similar function, can be used to prepare the aperture in the annulus. As a result, an aperture in the annular wall is created which is compatible with the configuration of the device. In the case of a disc which is compressed or has a weakened annular portion, one or more apertures can be provided in the portion(s) of the annulus that require the most structural support or adjustment.

Referring back to FIGS. 1 and 2, the device is positioned into the annular portion 3 of the intervertebral disc 2 at the desired tissue site. The implantation site can be the site of a herniation in the case of a herniated disc, or an otherwise damaged or attenuated annular portion of the disc. Typically, the posterior side, and more often the posterio-lateral side 7, of the intervertebral disc 2 is naturally susceptible to herniation and weakening from vertical compression on the disc, given the torsion movement and distribution of forces exerted caused by spinal compression. Damage to the annulus can also be a result of surgery, for example surgical access ports created for insertion of a prosthetic nucleus inside the disc.

Conventional arthroscopic instruments and techniques can be used to create the aperture through the annulus for the device. In one embodiment, the damaged portion of the annulus caused by herniation is removed using a trocar, laser knife and/or other instruments as can be needed. The use of a trocar is desirable since the diameter of the opening in the annulus which the trocar will create can be ascertained prior to implantation and the appropriate dimensions of the device pre-determined. Site preparation techniques for non-herniated discs for the device will not typically involve removal of exterior herniated tissue from the annulus as a first step.

The size of the opening in the annulus is selected according to the extent of damage caused by herniation, the circumferential or overall dimension of the device, discectomy techniques and instruments employed, or combinations thereof. For example, when used to repair damage to the annulus caused by herniation, the opening can contain a diameter sufficient to remove the ruptured and extruded tissue and create a substantially smooth interior surface in the opening. Preferably, the diameter does not exceed the height of the annulus so as to facilitate ingrowth by completely surrounding the device with existing annular tissue.

It should be understood that it is well within the level of ordinary skill in the art to coordinate the dimensions of the opening with those of the device and the annulus.

In addition to selecting specific trocar-type drill diameters, computer programs and other measurement techniques known to one of ordinary skill in the art can be used to aid the practitioner in assessing the dimensions of the prepared tissue site so as to properly configure the device.

The number and configuration of expandable devices used can be varied or altered according to the specific patient's needs. In order to optimize the compliancy of the device to the tissue site, the tissue aperture can itself be adjusted and/or the device can be molded or sculpted according to the aperture. Accordingly, if the damage to the annulus, for example, is more severe, expanding the width of the device to conform to the wider opening in the annulus may be desirable. As in the case of multiple herniations or access ports, more than one device can be implanted at the respective tissue sites, for example.

The device is preferably sterilized in the course of its manufacture and packaging, or prior to implantation. In the case of porous PVA having thermoplastic properties, the device can be sterilized by heat treatments or chemical methods of sterilization. With respect to heat treatments, the material can be suspended in boiling water or autoclaved at a suitable sterilizing temperature and pressure, noting that the material will permanently shrink to approximately 20% of the size after the treatment. For example, the material can be sterilized at a temperature of approximately 250° F. (about 121° C.) and at a pressure of about 15 psi. In order to avoid distortion, however, compressing or otherwise exerting physical force on the material during sterilization or subsequent cooling should be avoided. When immersed in water, the material should be immersed for a time period sufficient to allow the hot water to permeate the material, which depends largely upon the size of the material.

Placement of the device into the aperture can be accomplished by various means using a variety of surgical instruments and techniques. For example, implantation of the device can be performed by expanding the tissue surrounding the aperture, inserting the device into the aperture, and releasing the surrounding tissue thereby securing the device into place. Preferably, the immediate securing of the device in the aperture is accomplished by using a material which can be expandable in situ, upon hydration or release from constraining means.

Expansion kinetics can be controlled by various methods or systems, e.g. physical constraints, modification of chemical or structural properties of the material. When the device expands by way of hydration of the material, expansion can be regulated by higher molecular weight cross-linking of the exterior portion, mechanical compression, chemical additives or coatings, heat treatments, layering of materials, and the like.

Controlling expansion of the biomaterial used in the device offers several advantages. The ability to predict initial expansion time permits the practitioner to schedule the surgical procedure appropriately, as well as use the expansion of the implant to his or her best advantage, as well as benefit the patient. The timing of expansion can range from complete and immediate hydration during surgical implantation, gradually over a prolonged period of time, or suddenly at a later time. Given the present disclosure, those skilled in the art can select the appropriate method or treatment for controlling expansion according to the particular material used and the patient's needs.

The device can be inserted into the intervertebral region and positioned within the annulus using a suitable delivery apparatus, such as a cannula. The delivery device can comprise a delivery cannula having a longitudinally moveable expulsion rod therein so that the annular device can be contained in contracted form inside the distal portion of the cannula and expelled through the tip into the annular opening. Alternatively, the device can be implanted in a more direct manner in the absence of a cannula. The appropriate delivery method is selected by the practitioner depending upon the particular device configuration.

In addition to fixation brought about by the configuration (shape and dimensions), expansion and compliancy of the device, supplemental surgical fixation or securing of the device into position can be performed as well. A variety of techniques can be used in order to enhance short-term fixation of the device. Additional anchoring means can be used on the exterior surface of the device so as to affix the device into the annulus and prevent migration of the device. Examples of such anchoring means include, but are not limited to, polymeric meshes or tines for impregnation into the annulus. Examples of such surgical fixation techniques include, but are not limited to, biodegradable sutures, staples, fibrin sealants, surgical glues and the like. When suturing techniques are used to secure the device in the annulus, for example, the ends of the device can be sutured together with the adjacent annular tissue surrounding the aperture. Given the disclosure, the selection of an appropriate fixation method is well within the level of ordinary skill in the art.

The invention also discloses a method of repairing a tissue site, such as the annulus of an intervertebral disc, using the device described herein. According to such method, the tissue site is accessed, prepared, and the device inserted into the site using conventional arthroscopic surgical techniques. For example, the device can be contained within a cannula where upon positioning at the tissue site, the device is expelled from the cannula into position.

Another aspect of the invention relates to a method of repairing and supporting the intervertebral disc in a patient using the implantable annular device, including a method of repairing a herniated disc using the device. Yet another aspect of the invention invention relates to an intervertebral disc treated with the device and method of the invention.

The device of the invention can be included as a component of a surgical kit for implanting the device along with other surgical instruments or tools. Generally, the kit comprises the implantable tissue repair device according to the invention together with a minimally invasive delivery apparatus.

A preferred delivery apparatus includes a cannula adapted to both contain and position the expandable device in a minimally invasive fashion. The dimensions of the cannula are selected according to the specific features of the tissue site. Accordingly, the longitudinal dimension, curvature, width or circumference of the cannula can vary. The delivery apparatus can further comprise a placement feature for use in positioning the device. The placement tool can include an elongated rod having a plate attached to the distal tip adapted to be movably contained within the cannula. The movement of the elongated rod is controlled by the surgeon and can be in the form of a syringe-like structure, trigger, and the like. Accordingly, when pushed forward, the placement tool expels or ejects the tissue repair device from the distal end of the cannula into the biological aperture.

The kit can also include arthroscopic instruments adapted for use in preparing the tissue site or positioning the device.

Such instruments include, but are not limited to, laser knives, drill bits and trocars. The kit can also comprise sculpting or molding tools for modifying the configuration of the device according to the patient's particular needs, i.e. the delivery apparatus, the biological aperture within which the device is to be placed, predicted expansion parameters if material used in the device is expandable. Examples of sculpting tools include, but are not limited to, blades, burrs, scissors, and trocars.

Numerous characteristics and advantages of the invention covered by this document have been set forth in the foregoing description. It will be understood, however, that this disclosure is, in many respects, only illustrative. Changes can be made in details, particularly in matters of shape, size, and arrangement of components without exceeding the scope or departing from the spirit of the invention. The inventor's scope, of course, is defined in the language in which the appended claims are expressed.

What is claimed is:

1. A device for sealing a biological aperture in situ, the device comprising a porous, expandable material adapted to be sealably positioned within the biological aperture and to permit natural tissue ingrowth into the device, wherein the aperture is in the annulus of an intervertebral disc.

2. A device according to claim 1 wherein the material is adapted to be delivered to and positioned within the aperture, in conformity with the dimensions of the aperture, using minimally invasive techniques.

3. A device according to claim 2 wherein the porous material is adapted to become permanently secured over time, by permitting ingrowth of natural fibrous tissue into some or all of the pores.

4. A device according to claim 3 wherein ingrowth is facilitated by incorporating a bioactive agent into the material.

5. A device according to claim 2 wherein the material is expandable, such that once positioned the material can swell in order to initially secure the expanded device within the aperture.

6. A device according to claim 5 wherein the material comprises poly(vinyl alcohol).

7. A device according to claim 1 wherein the device is provided in a configuration selected from the group consisting of cylindrical plugs, tubular forms, and elongated, curved forms.

8. A device according to claim 7 wherein the device is provided in an elongated, curved configuration having first and second ends adapted for insertion into a plurality of apertures within an annulus.

9. A device according to claim 7 wherein the device is adapted to be used in combination with a biomaterial delivery cannula, in order to seal the cannula access aperture formed in the annulus in the course of delivering a curable biomaterial to the nucleus.

10. A method for sealing a biological aperture in situ, the method comprising the use of a device comprising a porous, expandable material adapted to be sealably positioned within the biological aperture and to permit natural tissue ingrowth into the device, wherein the aperture is in the annulus of an intervertebral disc.

11. A method according to claim 10 wherein the porous material is adapted to become permanently secured over time, by permitting ingrowth of natural fibrous tissue into some or all of the pores.

12. A method according to claim 11 wherein ingrowth is facilitated by incorporating a bioactive agent into the material.

13. A method according to claim 10 wherein the material is expandable, such that once positioned the material can swell in order to initially secure the expanded device within the aperture.

14. A method according to claim 13 wherein the material comprises poly(vinyl alcohol).

15. A method according to claim 10 wherein the device is provided in an elongated, curved configuration having first and second ends adapted for insertion into a plurality of apertures within an annulus.

16. A surgical kit comprising a device according to claim 1 in combination with a surgical tool adapted to insert and position the device within a biological aperture.

17. A surgical kit comprising a plurality of devices, each according to claim 1, wherein each device is provided in a different configuration for selection and use in the course of surgery.

18. A device according to claim 1 wherein the device comprises regions of varying chemical and/or physical properties.

19. A device according to claim 18 wherein the regions are provided in the form of internal and external portions wherein the internal portion is provided in the form of a semi-rigid material used to provide mechanical support.

20. A device according to claim 1, further comprising a substance to enable external imaging of the device.

21. A device according to claim 20 wherein the substance comprises a radio-opaque material suitable to permit imaging by MRI or X-ray.

22. A device according to claim 1 wherein the aperture is provided in the form of an orifice, hole, cleft, or tear in a biological tissue.

23. A device for sealing a biological aperture in situ, the device comprising a porous, expandable material adapted to be sealably positioned within a biological aperture and to permit natural tissue ingrowth into the device, wherein the aperture is provided in the annulus of an intervertebral disc, the material comprises poly(vinyl alcohol), and the device is adapted to be delivered to and positioned within the aperture, in conformity with the dimensions of the aperture, using minimally invasive techniques.

24. A device according to claim 23 wherein the aperture is in the annulus of an intervertebral disc, and the device is provided in a configuration selected from the group consisting of cylindrical plugs, tubular forms, and elongated, curved forms.

25. A device according to claim 1 wherein the porous, expandable material is selected from the group consisting of natural and synthetic polymers, including co-polymers and combinations thereof, processed into the form of porous matrices or foams.

26. A device according to claim 25 wherein the material is selected from the group consisting of synthetic non-biodegradable polymers, synthetic biodegradable polymers, and natural biodegradable polymers.

27. A device according to claim 26 wherein the material comprises a synthetic non-biodegradable polymer selected from the group consisting of polyvinyl alcohol, polyethylene, polyurethane, polypropylene, polycaprolactone, polyacrylates, ethylene-vinyl acetates, polystyrenes, polyvinyl oxides, polyvinyl fluorides, poly(vinyl imidazoles), chlorosulphonated polyolefins, polyethylene oxides, polytetrafluoroethylenes and nylons, and copolymers and combinations thereof.

28. A device according to claim 27 herein the polymer comprises polyvinyl alcohol and alkylated or acylated derivatives thereof.

29. A device according to claim 26 wherein the material comprises a synthetic biodegradable polymer selected from the group consisting of polylactides, polyglycolic acids, poly(lactide-co-glycolides), polycaprolactones, polycarbonates, polyamides, polyanhydrides, polyamino acids, polyortho esters, polyacetals, polycyanoacrylates, and degradable polyurethanes.

30. A device according to claim 26 wherein the material comprises a natural biodegradable polymer selected from the group consisting of albumin, collagen, synthetic polyamino acids, prolamines, and polysaccharides.

31. A device according to claim 5 wherein the material is provided in a contracted or unexpanded form, and is expandable, in situ upon implantation, by either hydration or release from constraining means.

32. A device according to claim 25 wherein the material is adapted to be secured or anchored into the aperture using biodegradable sutures, staples, fibrin sealants, or surgical glues.

33. A device according to claim 25 wherein the material provides a pore size range from about 50 microns to about 500 microns.

34. A device according to claim 33 wherein the pore size range is from about 100 to about 300 microns.

35. A device according to claim 25 wherein the material is provided in the form of a fibrous matrix.

36. A device according to claim 35 wherein the space between fibers is in the range of from about 10 microns to about 1000 microns.

37. A device according to claim 1 wherein the device further comprises a bioactive agent selected from the group consisting of growth factors, angiogenic factors, immune system suppressors, antibiotics, living cells, and cell-binding proteins and peptides.

38. A device according to claim 37 wherein the device comprises a growth factor selected from the group consisting of somatomedins, insulin-like growth factors, fibroblast growth factors, bone morphogenic growth factors, endothelial growth factors, transforming growth factors, platelet derived growth factors, hepatocytic growth factors, keratinocyte growth factors, and combinations thereof.

39. A device according to claim 37 wherein the device comprises living cells selected from the group consisting of fibroblasts, chondrocytes, chondroblasts, osteocytes, mesenchymal cells, epithelial cells, and endothelial cells.

40. A device according to claim 37 wherein the device comprises cells obtained by allograft or autograft cell culture.

41. A method according to claim 10 wherein the device comprises regions of varying chemical and/or physical properties.

42. A method according to claim 41 wherein the regions are provided in the form of internal and external portions wherein the internal portion is provided in the form of a semi-rigid material used to provide mechanical support.

43. A method according to claim 10 where in the device further comprises a substance to enable external imaging of the device.

44. A method according to claim 43 wherein the substance comprises a radio-opaque material suitable to permit imaging by MRI or X-ray.

45. A method according to claim 10 wherein the aperture is provided in the form of an orifice, hole, cleft, or tear.

46. A method according to claim 10 wherein the porous, expandable material is selected from the group consisting of natural and synthetic polymers, including co-polymers and combinations thereof, processed into the form of porous matrices or foams.

47. A method according to claim 46 wherein the material is selected from the group consisting of synthetic non-biodegradable polymers, synthetic biodegradable polymers, and natural biodegradable polymers.

48. A method according to claim 47 wherein the material comprises a synthetic non-biodegradable polymer selected from the group consisting of polyvinyl alcohol, polyethylene, polyurethane, polypropylene, polycaprolactone, polyacrylates, ethylene-vinyl acetates, polystyrenes, polyvinyl oxides, polyvinyl fluorides, poly (vinyl imidazoles), chlorosulphonated polyolefins, polyethylene oxides, polytetrafluoroethylenes and nylons, and copolymers and combinations thereof.

49. A method according to claim 48 herein the polymer comprises polyvinyl alcohol and alkylated or acylated derivatives thereof.

50. A method according to claim 47 wherein the material comprises a synthetic biodegradable polymer selected from the group consisting of polylactides, polyglycolic acids, poly(lactide-co-glycolides), polycaprolactones, polycarbonates, polyamides, polyanhydrides, polyamino acids, polyortho esters, polyacetals, polycyanoacrylates, and degradable polyurethanes.

51. A method according to claim 47 wherein the material comprises a natural biodegradable polymer selected from the group consisting of albumin, collagen, synthetic polyamino acids, prolamines, and polysaccharides.

52. A method according to claim 13 wherein the material is provided in a contracted or unexpanded form, and is expandable, in situ upon implantation, by either hydration or release from constraining means.

53. A method according to claim 46 wherein the material is adapted to be secured or anchored into the aperture using biodegradable sutures, staples, fibrin sealants, or surgical glues.

54. A method according to claim 46 wherein the material provides a pore size range from about 50 microns to about 500 microns.

55. A method according to claim 54 wherein the pore size range is from about 100 to about 300 microns.

56. A method according to claim 46 wherein the material is provided in the form of a fibrous matrix.

57. A method according to claim 56 wherein the space between fibers is in the range of from about 10 microns to about 1000 microns.

58. A device according to claim 1 wherein the device further comprises a bioactive agent selected from the group consisting of growth factors, angiogenic factors, immune system suppressors, antibiotics, living cells, and cell-binding proteins and peptides.

59. A device according to claim 58 wherein the device comprises a growth factor selected from the group consisting of somatomedins, insulin-like growth factors, fibroblast growth factors, bone morphogenic growth factors, endothelial growth factors, transforming growth factors, platelet derived growth factors, hepatocytic growth factors, keratinocyte growth factors, and combinations thereof.

60. A device according to claim 58 wherein the device comprises living cells selected from the group consisting of fibroblasts, chondrocytes, chondroblasts, osteocytes, mesenchymal cells, epithelial cells, and endothelial cells.

61. A device according to claim 58 wherein the device comprises cells obtained by allograft or autograft cell culture.

\* \* \* \* \*